United States Patent [19]

Adam et al.

[11] Patent Number: 4,871,578
[45] Date of Patent: Oct. 3, 1989

[54] HYDROXYLAPATITE COATING ON METAL OR CERAMIC

[75] Inventors: Peter Adam, Dachau; Adolf Nebelung, Ketsch; Michael Vogt, Moerlenbach, all of Fed. Rep. of Germany

[73] Assignees: MTU Motoren- und Turbinen-Union Muenchen GmbH, Munich; Benckiser-Knapsack GmbH, Ladenburg, both of Fed. Rep. of Germany

[21] Appl. No.: 177,246

[22] Filed: Apr. 4, 1988

[30] Foreign Application Priority Data

Apr. 4, 1987 [DE] Fed. Rep. of Germany ....... 3711426

[51] Int. Cl.$^4$ .................... B05D 1/10; A61C 13/30; A61F 1/64
[52] U.S. Cl. .................... 427/2; 204/192.1; 427/248.1; 427/423; 623/16; 623/20; 623/22
[58] Field of Search .................... 427/2, 248.1, 423; 623/20, 22, 23, 16; 433/201.1, 226, 228.1; 204/192.1

[56] References Cited

U.S. PATENT DOCUMENTS

| 4,548,959 | 10/1985 | Nagai et al. ........... | 433/201.1 |
| 4,645,503 | 2/1987 | Lin et al. .............. | 623/16 |
| 4,687,675 | 8/1987 | Nakano et al. .......... | 427/2 |
| 4,705,694 | 11/1987 | Buttazzoni et al. ..... | 427/2 |

FOREIGN PATENT DOCUMENTS

| 2733394 | 2/1979 | Fed. Rep. of Germany . |
| 2824118 | 12/1979 | Fed. Rep. of Germany . |
| 3034086 | 3/1982 | Fed. Rep. of Germany . |
| 3316801 | 11/1984 | Fed. Rep. of Germany . |
| 3414992 | 10/1985 | Fed. Rep. of Germany . |

OTHER PUBLICATIONS

P. Adam, "Biokompatible und bioaktive Beschichtungen", Fortschr. Zahnarztl. Implant. 1, 41–46/1984, pp. 41–43.

Nebelung, et al., "Uber die Eigenschaften von Calciumphosphaten im Hinblick auf ihre Verwendung in der Biokeramik," Sprechsaal, vol. 119, No. 12, 1986, pp. 1131–1134.

*Primary Examiner*—Michael Lusignan
*Attorney, Agent, or Firm*—Foley & Lardner, Schwartz, Jeffery, Schwaab, Mack, Blumenthal & Evans

[57] ABSTRACT

A process for the production of a layer of hydroxyapatite (HA) on metallic and non-metallic bodies for implants is disclosed, wherein a layer of α- or β-tricalcium phosphate (TCP) is applied and this is then completely converted into pure HA by reaction with water at an elevated temperature.

10 Claims, 2 Drawing Sheets

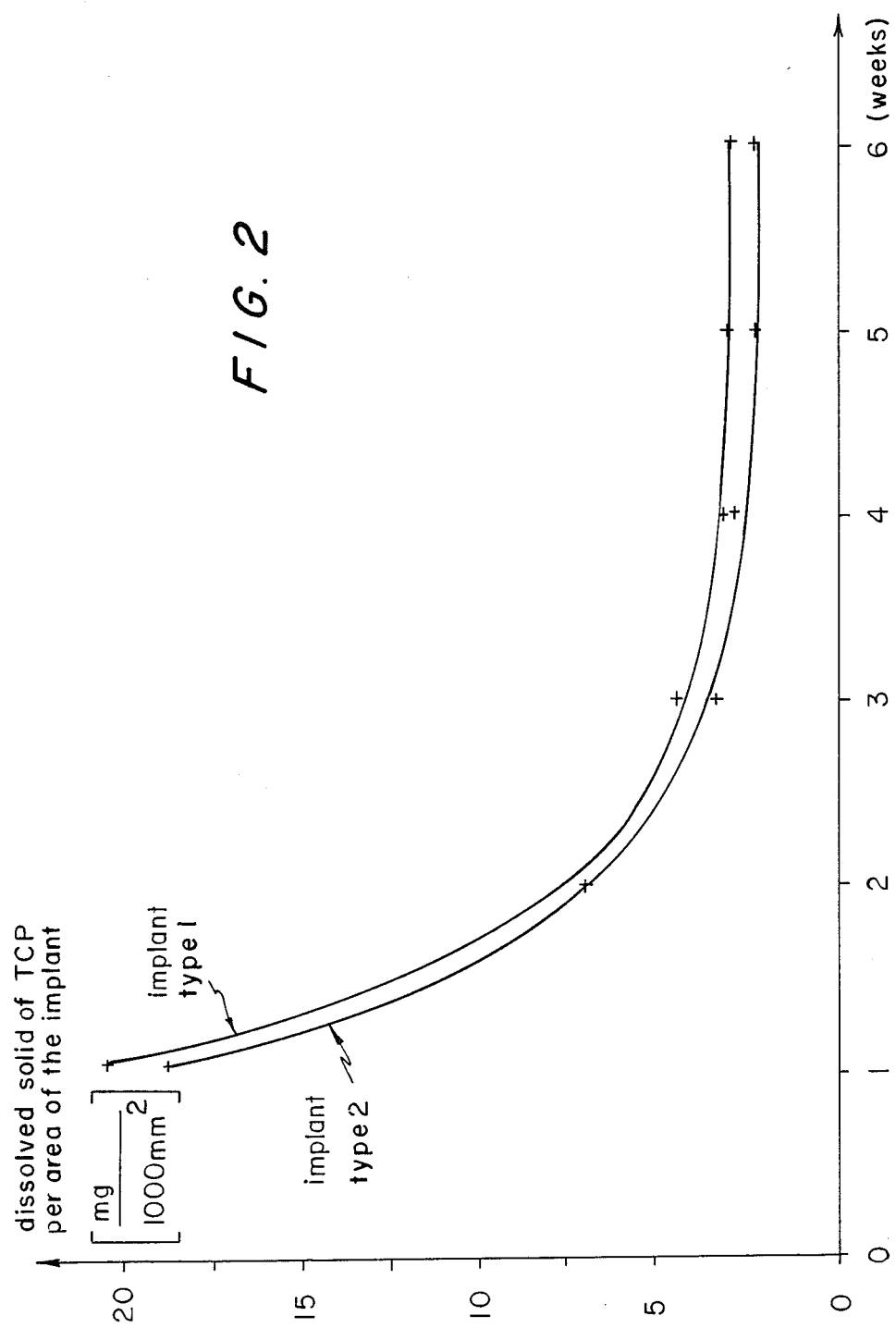

HYDROXYLAPATITE COATING ON METAL OR CERAMIC

BACKGROUND OF THE INVENTION

The present invention relates to a process for coating metallic or ceramic bone replacement parts or dental replacement parts with bioactive substances.

Bioactive substances assist at least partly in the promotion of the growth of the implants on the bone structure in the body. By means of this growth, an implant anchored only purely mechanically in the bones is avoided. As a result, the implant is not subject to any rejection reaction, i.e., it is tissue-compatible, and the connection to the bones is stressable which means that the implant can remain in the body for a sufficient period of time.

According to the present state of knowledge, tricalcium phosphate (TCP) and hydroxylapatite (HA) are particularly suitable as bioactive substances, with HA being preferred.

Implants are already known which partly carry a coating with particles of calcium phosphate, for example from Federal Republic of Germany Patent Specifications Nos. 27 33 394, 28 24 118 and 30 34 086. In Federal Republic of Germany Patent Specification Nos. 33 16 801 and 34 14 992, hydroxylapatite and tricalcium phosphate are mentioned as bioactive materials. However, in both of these references, special measures are mentioned which ensure a firm and secure growth of the implant with the surrounding tissue.

The application of thin layers of ceramic material to metal surfaces is, in principle, known (cf., for example P. Adam, Fortschr. Zahnarztl. Implant., 1, 41-46/1984).

Furthermore, "Sprechsaal," 119, (12), 1131-1134/1986, discloses that all tricalcium phosphates rearrange in water into hydroxylapatite. It is suggested, for the use of calcium diphosphate as an intermediate layer between implant and tissue, to apply a base layer of dicalcium phosphates, which are practically insoluble in water and a surface layer of $\beta$-tricalcium or a mixture of $\alpha$- and $\beta$-tricalcium phosphate. The assumption is made that once implanted, the calcium phosphates on the surface are converted into hydroxylapatite. Corresponding layers can only be produced with difficulty and they are not reproducible and stable.

If it is desired to produce satisfactorily adhering layers on the implant, which can be grown on and can bear loads, then it has proved useful, in addition to selecting appropriate materials, to control the production and sinter conditions of the layer. The porosity of, for example, a sintered-apatite material can also be controlled in this way. In the case of the temperatures necessary for sintering, a partial decomposition of the HA takes place, with the loss of its water of constitution, to give tricalcium and tetracalcium phosphate, so that a pure hydroxylapatite is no longer present and the resultant layers are no longer optimal for the growing on of the implant.

SUMMARY OF THE INVENTION

It is an object of the present invention to provide a process for the production of a pure, non-porous hydroxylapatite layer.

These and other objects, according to the present invention, are provided by a process for the production of a layer of hydroxylapatite (HA) on metallic and non-metallic bodies for implants, wherein a layer of $\alpha$- or $\beta$-tricalcium phosphate (TCP) is applied, and this is then completely converted into pure HA by reaction with water at an elevated temperature.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWING

FIGS. 1 and 2 show the decrease of tricalcium phosphate (TCP) solubility.

DETAILED DESCRIPTION OF THE PREFERRED EMBODIMENTS

Figure 1:
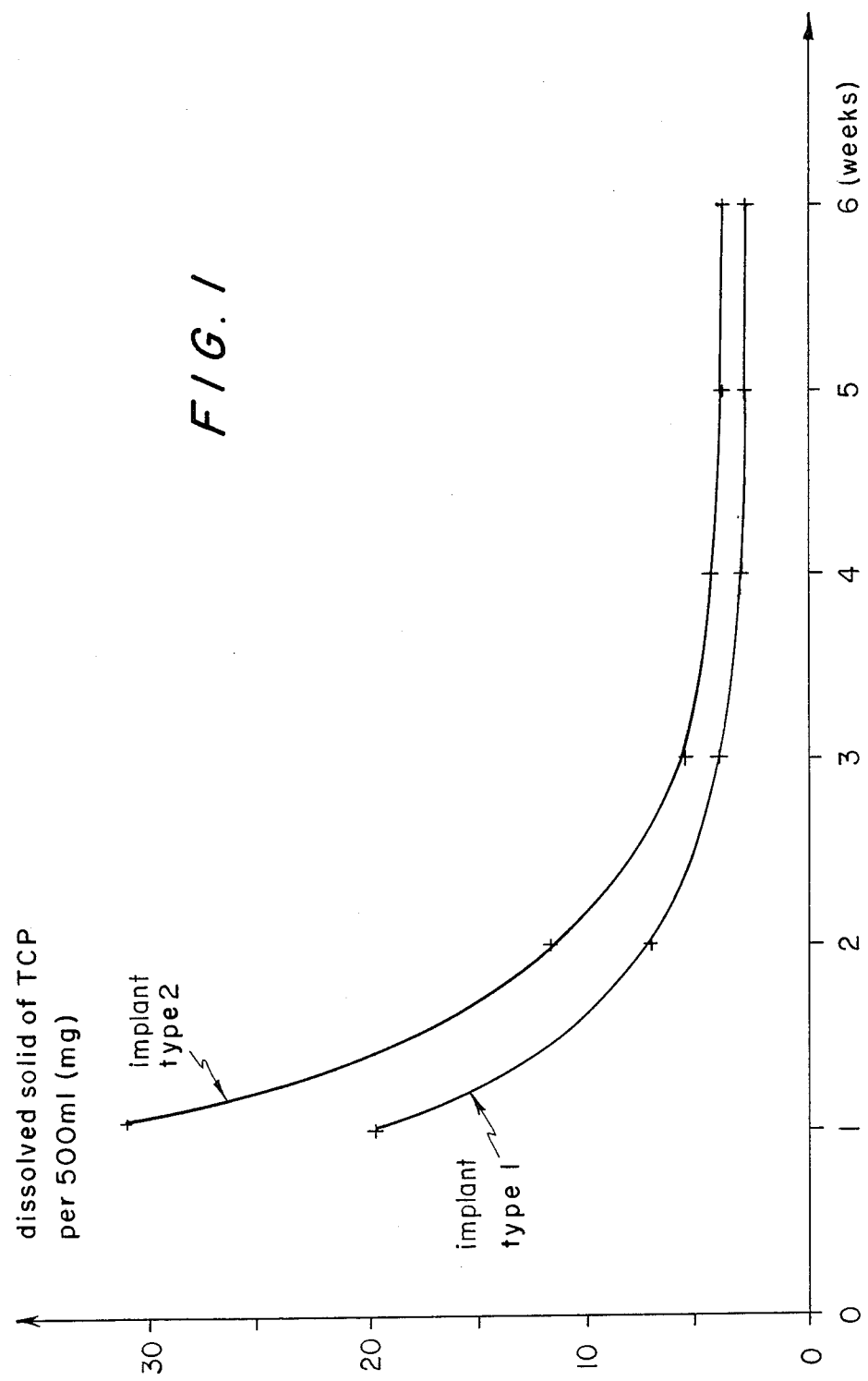

The process according to the present invention is preferably carried out at a temperature of from about 80° to 100° C. in an aqueous phase with a pH of from about 2 to 7.

The layer initially applied preferably consists of $\alpha$-TCP.

The present invention also includes combinations of the conversion process with layer production processes, as well as the use of such layers on implants, especially dental implants and endossal implants, such as hip joint bones and knee joints, and also on protheses and partial protheses.

With the present invention, the following advantages in particular are achieved. Calcium phosphate layers can be applied at high temperatures at which hydroxylapatite would otherwise decompose. As a result, dense layers, i.e., layers of low porosity, can be produced. The layers converted into hydroxylapatite are very tissue compatible and permit a more rapid resorption and healing in. Even under stress, the new implants can remain in the body for comparatively long periods of time.

In order to obtain an HA layer, pure TCP is first applied, for example by thermal spraying, vacuum deposition or sputtering, in an appropriate, known device. A sufficiently dense, pure TCP layer is thereby obtained without decomposition products. If, due to high cooling rates, $\alpha$-TCP (high temperature modification) results, then $\beta$-TCP can be produced therefrom by subsequent heat treatment.

The $\alpha$- or $\beta$-TCP layer so obtained on the implant is completely converted into HA by heating the implants in water. The water temperature is adjusted according to the possibilities of the apparatus. The rate of reaction of the conversion of the TCP layer into an HA layer is a function of the temperature. The higher the temperature selected, the more quickly the conversion takes place. However, it is to be taken into account that the amount dissolved in the water also increases with increasing temperature. The most preferred temperature range is from about 60° to 90° C.

The following examples are given for the purpose of illustrating the present invention and are non-limiting:

EXAMPLE 1

Production of the coatings.

Cylindrical standard bodies of titanium with lengths of 8.0 cm (type I) and 12.5 cm (type II) and a diameter of 4.0 cm, i.e., a surface area of 113 and 170 cm$^2$, respectively, are carefully polished in order to remove the superficial oxide layer and cleaned with dilute hydrochloric acid and alcohol. It is assumed that, even after this treatment, a titanium dioxide layer of from 0.01–0.02 μm still remains on the surface.

Several layers of β-tricalcium phosphate are applied on these bodies by a plasma spray method until an approximately 180 μm thick, firm and uniform layer is obtained. According to X-ray diffractograms, the layer formed consists of the pure high temperature form, i.e., α-TCP. Stereomicroscopic investigations show that the layer is smooth and without cracks or pores.

By means of a comparatively long heat treatment, the α-TCP can be converted back into β-TCP. Since the solubility of both phases is about the same, further working is carried out with the originally formed α-TCP layer.

EXAMPLE 2

Conversion of the TCP layer into HA.

Eight bodies of type I or type II are placed in the paper cartridge of a Soxhlet apparatus (volume about 70 ml) and 450 ml of distilled water are placed in the distillation flask. The number of recyclings is 7.5 per hour and the average temperature of the cartridge is 80° C.

The conversion of TCP into HA is monitored on the basis of the amount of phosphate going into solution per unit time, which becomes enriched in the distillation flask. The amount of phosphate is, for this purpose, determined photometrically at weekly intervals.

FIGS. 1 and 2 of the accompanying drawings show the decrease of TCP solubility, in which case, after about 4 to 6 weeks, the practically negligible solubility of the HA is obtained (about 2 mg/1000 ml per week).

X-ray diffractograms of the coating material scraped off from the titanium bodies show that the TCP has been completely converted into HA. Stereomicroscopic pictures show that the converted layer is still smooth and without cracks or pores.

The above experiment was repeated, the TCP-coated bodies thereby being boiled directly in 0.1 molar hydrochloric acid. The conversion into HA due to the elevated temperature and possibly due to the addition of hydrochloric acid was achieved after 10 to 20 days.

What is claimed is:

1. A process for the production of a layer of hydroxylapatite (HA) on metallic and non-metallic bodies for implants, comprising the steps of:
    applying a layer of α- or β-tricalcium phosphate (TCP);
    completely converting said layer into pure HA by reaction with water at an elevated temperature.

2. A process according to claim 1, wherein the converting step is carried out at a temperature of from 80° to 100° C.

3. A process according to claim 1, wherein the aqueous phase has a pH value of from about 2 to 7.

4. A process according to claim 1, wherein the layer applied in the first step consists essentially of α-TCP.

5. A process according to claim 1, wherein the TCP layer is applied by thermal spraying, vacuum deposition or sputtering with α- or β-TCP.

6. A process according to claim 2, wherein the layer consists of α-TCP.

7. A process according to claim 2, wherein the water has a pH from about 2 to 7.

8. A process according to claim 7, wherein the layer applied in the first step consists essentially of α-TCP.

9. A process according to claim 1, consisting essentially of the recited steps.

10. An implant produced by the process according to claim 1.

* * * * *